(12) United States Patent
Frankena et al.

(10) Patent No.: US 9,233,865 B2
(45) Date of Patent: Jan. 12, 2016

(54) BIOREACTOR COMPRISING A MIXING CHAMBER

(75) Inventors: Douwe Frankena, Bolsward (NL); Sjoerd Hubertus Jozef Vellinga, Tjalleberd (NL)

(73) Assignee: PAQUES I.P. B.V. (NL)

( * ) Notice: Subject to any disclaimer, the term of this patent is extended or adjusted under 35 U.S.C. 154(b) by 232 days.

(21) Appl. No.: 13/318,605

(22) PCT Filed: May 3, 2010

(86) PCT No.: PCT/NL2010/050254
§ 371 (c)(1),
(2), (4) Date: Jan. 19, 2012

(87) PCT Pub. No.: WO2010/128850
PCT Pub. Date: Nov. 11, 2010

(65) Prior Publication Data
US 2012/0115218 A1     May 10, 2012

(30) Foreign Application Priority Data

May 4, 2009   (EP) ..................... 09159341

(51) Int. Cl.
| | |
|---|---|
| *C12M 3/00* | (2006.01) |
| *C12M 1/00* | (2006.01) |
| *C02F 3/28* | (2006.01) |
| *C12M 1/02* | (2006.01) |

(52) U.S. Cl.
CPC .............. *C02F 3/2846* (2013.01); *C12M 23/34* (2013.01); *C12M 27/00* (2013.01); *C02F 3/2853* (2013.01); *C02F 2203/006* (2013.01); *Y02W 10/12* (2015.05)

(58) Field of Classification Search
CPC ...... C12M 27/22; C12M 27/18; C12M 29/06; C12M 29/14
See application file for complete search history.

(56) References Cited

U.S. PATENT DOCUMENTS

| | | | |
|---|---|---|---|
| 4,202,774 A | | 5/1980 | Kos |
| 4,426,450 A | * | 1/1984 | Donofrio ...................... 435/243 |
| 4,707,252 A | * | 11/1987 | Durot et al. ................... 210/151 |

(Continued)

FOREIGN PATENT DOCUMENTS

| | | |
|---|---|---|
| CA | 1212790 | 10/1986 |
| CN | 101092268 | 6/2007 |

(Continued)

OTHER PUBLICATIONS

Patent Cooperation Treaty (PCT), International Search Report, Jul. 21, 2010, 3 pages.

*Primary Examiner* — Nathan Bowers
(74) *Attorney, Agent, or Firm* — Tucker Ellis LLP (57) ABSTRACT

The invention relates to a bioreactor (1) comprising a reactor vessel (41) having a mixing chamber (3) separated by a partition (44) from a reaction chamber (2) located generally above the mixing chamber (3), the mixing chamber (3) having an inlet system (4) for influent or a mixture of influent and recycled material, wherein the inlet system (4) has an outlet opening (60-64) in the mixing chamber (3). In an embodiment the partition (44) has an opening (66) forming a connection between the mixing chamber (3) and the reaction chamber (2), wherein the outlet opening (60-64) of the inlet system (4) is directed at the opening in the partition. In an embodiment the mixing chamber (3) has a skeleton for reinforcing the mixing chamber.

17 Claims, 3 Drawing Sheets

(56) References Cited

U.S. PATENT DOCUMENTS

| | | | | |
|---|---|---|---|---|
| 5,338,447 | A | * | 8/1994 | Vellinga ................ 210/195.1 |
| 6,063,273 | A | * | 5/2000 | Habets et al. ............ 210/188 |
| 6,602,416 | B1 | * | 8/2003 | Rossmanith ............. 210/603 |

FOREIGN PATENT DOCUMENTS

| | | |
|---|---|---|
| CN | 101007680 | 8/2007 |
| DE | 3623431 | 1/1988 |
| EP | 0539430 | 5/1993 |
| EP | 91912937.9 | 10/1994 |
| JP | 63305993 | 12/1988 |
| JP | 2007029109 | 4/1995 |
| JP | 2001507619 | 6/2001 |
| JP | 2001276856 | 10/2001 |
| RU | 2060964 | 5/1996 |
| RU | 2139132 | 10/1999 |
| RU | 2344998 | 1/2009 |
| WO | 92/01637 | 2/1992 |
| WO | 2010128851 | 11/2010 |

* cited by examiner

BIOREACTOR COMPRISING A MIXING CHAMBER

CLAIM OF PRIORITY

The present application is a 371 of International Patent Application No. PCT/NL2010/050254, by Frankena, et al., filed May 3, 2010, which claims priority to European Patent Application No. EP09159341.8 filed May 4, 2009; which applications are herein incorporated by reference.

TECHNICAL FIELD

The invention relates to a bioreactor comprising a reactor vessel having a mixing chamber separated by a partition from a reaction chamber located generally above the mixing chamber. The invention further relates to a method of mixing influent in a reactor vessel.

BACKGROUND OF THE INVENTION

From EP 0 539 430-B1 a bioreactor is known having a reaction chamber and a mixing chamber. An inlet system allows influent and/or recycled material to enter the reactor vessel through a mixing chamber separated from the reaction chamber by a partition, the partition having slits. The mixing chamber is conically shaped and comprises steel plates welded to the interior of the reactor vessel near a bottom thereof. The inlet system provides a tangential flow in the mixing chamber.

Much of the energy necessary to bring the influent and/or recycled material in the mixing chamber is dissipated with the cyclone flow in the mixing chamber according to EP 0 539 430-B1. Still, the pressure difference over the partition is limited because of strength limitations of the partition material which causes unequal distribution of the influent in the mixing chamber and eventually in the reaction chamber. Further the pressure difference over the partition increases the level in the degassing tank connected downstream with the bioreactor.

SUMMARY

In accordance with an embodiment, a bioreactor includes a reactor vessel having a mixing chamber separated by a partition from a reaction chamber located generally above the mixing chamber. The mixing chamber has an inlet system for influent and/or a mixture of influent and recycled material, wherein the inlet system has outlet openings in the mixing chamber. The partition has openings forming a connection between the mixing chamber and the reaction chamber, wherein the outlet opening of the inlet system is directed at the opening in the partition.

DETAILED DESCRIPTION OF THE DRAWINGS

It is a goal of the present invention to reduce at least one of these problems. This is achieved by providing a bioreactor comprising a reactor vessel having a mixing chamber separated by a partition from a reaction chamber located generally above the mixing chamber. In an embodiment the mixing chamber has an inlet system for influent and/or a mixture of influent and recycled material, wherein the inlet system has outlet openings in the mixing chamber. In an embodiment the partition has openings forming a connection between the mixing chamber and the reaction chamber, wherein the outlet opening of the inlet system is directed at the opening in the partition.

This will allow the flow of influent into the mixing chamber to be directed at openings through the partition and into the reaction chamber. Inflow energy is used directly for providing a flow from the mixing chamber into the reaction chamber. It also allows to reduce the overpressure in the mixing chamber, which allows lower costs by using less material for the partition between the mixing chamber and reaction chamber. This allows a saving in material and a reduction in costs.

In an embodiment the outlet opening is aligned with the opening in the partition. This will further reduce the resistance of a flow from the inlet system through the mixing chamber into the opening and into the reaction chamber.

Preferably outlet openings of the influent inlet system are directed at and/or aligned with the openings in the partition. This construction allows using an inlet system having a smaller pump with lower power is needed.

In an embodiment at least four outlet openings of the inlet system are directed at, or aligned with, at least four respective openings in the partition. By providing multiple openings a further reduction of the flow resistance is achieved.

In an embodiment the outlet opening has a nozzle comprising a surface area reduction of the inlet system. The inlet system comprises pipes for providing the influent into the mixing chamber. The influent exits the pipes through a nozzle, said nozzle providing a surface area reduction, which will allow a flow acceleration and pressure reduction. According to the invention the accelerated flow is directed at the openings through the partition.

Preferably the reduction is at least 25%. This will ensure sufficient acceleration. Further the accelerated flow will provide impulse to fluid surrounding the flow and will subsequently accelerate said fluid.

In an embodiment a surface area of the outlet opening is at least 20% and preferably at least 40% less than a surface area of the opening in the partition, the opening at which the outlet opening is directed. In such a relationship the flow directed from the outlet opening into the opening will pull fluid from the mixing chamber through the opening in the partition. The inflow energy is in this manner also used for mixing the influent with the fluid already present in the mixing chamber.

Preferably a distance between the outlet opening of the inlet system and the opening in the partition is less than eight times, preferably less than five times a width of the cross section of the outlet opening. The free distance or flow path of flow between the outlet opening of the inlet system and the opening in the partition has a limited length in order to prevent dissipation of the inflow energy and to further reduce the overpressure. Still this free distance allows drawing in fluid from the mixing chamber with the flow directed toward the opening in the partition.

In a further embodiment the distance between the outlet opening and the opening in the partition is variable. In an embodiment the opening and/or the outlet opening of the inlet system are moveably mounted in the bioreactor allowing varying of the free distance of flow between the two openings. In an embodiment the opening is moved using an actuator. In an embodiment the actuator is controlled using a central processor allowing a user to control and configure the free distance which provides the user with control over a parameter for controlling the amount of mixing in the mixing chamber.

In an embodiment the opening in the partition comprises a tube or pipe extending from one side of the partition through the partition and out of the other side of the partition. The tube provides a distance between a wall part of the partition and the openings of the tube. The openings of the tube or pipe are, as a result of extending from the partition, preferably a plate, not disturbed by for example sludge collecting on the partition that could for example block part of the opening. The blocking sludge is transferred over the tube around the opening.

In an embodiment the opening in the partition is positioned close to a reactor bottom of the reactor vessel. As sludge is collected in the reaction chamber and sinks as a result of higher density to the bottom of the reactor bottom, the inflow of influent and the energy of the inflow provided by the inlet system is used to disturb the collected sludge, which will result in better mixing and improved cleaning of the influent.

In an embodiment the mixing chamber further comprises outflow openings of the influent inlet system that are at least partially tangentially oriented with respect to an outflow opening for a mixture of influent and recycled material, such as a downer. This will allow the mixing of the recycled material in the mixing chamber, wherein said mixing comprises a circumferential flow around the outflow opening for the mixture of influent and recycled material, such as the downer. Preferably the downer is connected to a roof part or top part of the mixing chamber and comprises an opening in the partition wherein a tube of the downer is received. In an embodiment the outflow opening for the mixture is located in a top section of the mixing chamber, while openings through the partition are located near a bottom section of the mixing chamber. The mixture of influent and recycled material will reach the openings through the partition only after sufficient mixing in the mixing chamber.

In an embodiment the partition comprises a side wall of the mixing chamber having an opening in said side wall, wherein said side wall is oblique or skewed with respect of to a bottom of the reactor vessel. The oblique side wall prevents sludge deposition, preferably if the tilt is more than 45°.

In a further embodiment the mixing chamber is positioned on a reactor bottom of the reactor vessel and openings in the partition are directed generally parallel to the reactor bottom. The openings are directed outwards from the mixing chamber. The inflow energy is directed outward from the mixing chamber and is dissipated over the bottom of the reactor vessel allowing 'swirling' of sludge that would deposit on the bottom.

In a further embodiment the mixing chamber comprises at least six openings in the partition directed outwardly from the mixing chamber in four mutually generally perpendicular directions. This allows outward distribution of the mixed influent flow in all four wind directions. Preferably this will allow using a mixing chamber of limited size, covering only a portion of the reactor bottom, wherein the higher sludge concentration is swirled due to the energy of the inflow directed into the reaction chamber.

According to a further aspect a method of mixing an influent in a reactor vessel of bioreactor is provided. In an embodiment of the method a mixing chamber is provided separated by a partition from a reaction chamber in the reactor vessel, said reaction chamber located generally above the mixing chamber. Influent is fed into the mixing chamber. Further mixtures of influent and recycled material are received in the mixing chamber. A flow of recycled material can be fed to the mixing chamber using a downer. According to an embodiment a flow of fluid is provided from the mixing chamber to the reaction chamber through an opening in the partition. According to a preferred embodiment the influent feed is directed towards the opening in the partition. This will reduce the amount of dissipated energy of the fed influent on its path from the influent inlet system to the reaction chamber.

The invention relates to a bioreactor comprising a reactor vessel having a mixing chamber separated by a partition from a reaction chamber located generally above the mixing chamber.

Bioreactors require some sort of an influent inlet system to bring the influent or wastewater that is to be recycled into the reactor. It is known, for example from EP0539430B1, that it is advantageous to first bring the influent into an mixing chamber inside the reactor vessel, where the influent is mixed with already partially recycled material. Then the mixture of influent and recycled material is brought into the reaction chamber proper.

The mixing chamber, and therefore the point where the mixture of material to be recycled is inserted into the reaction chamber, may be located at the bottom of the reaction. Heavy sludge particles and solid contaminations will tend to sink to the bottom of the reactor while cleaner fluids can be found higher in the reactor column, so that influent materials should initially be inserted close to the bottom and then be allowed to rise as they are processed. For this reason, bioreactor vessels are typically shaped as cylinders, with the longitudinal axis oriented in the direction of gravity. However, other vessels shapes are possible.

A consequence of the sinking of heavier material is that at the bottom of the reactor vessel contaminated sludge will settle. A certain amount of biomass is needed for the working of the bioreactor, but excess amounts have to be removed, for example through a sludge discharge system.

It is a problem that the sludge in the bioreactor weighs down on the partition that separates the mixing chamber from the reaction chamber. It is known that this problem may be overcome by constructing the mixing chamber from rigid materials, such as steel, but the disadvantage is increased cost. It would be much more cost effective to use a synthetic material, such as a plastic, to form the partition with, but the weight of sludge on top of known mixing chambers makes this use impractical.

Known mixing chambers typically occupy all or most of the reactor vessel floor area. Constructing these mixing chambers typically involve welding connections to the sides of the reactor vessel. As such, these connections are expensive to make. A further disadvantage is that the design of the reactor vessel is influenced by the design and manufacture of the mixing chamber. This makes the use of industrially available standard vessels for bioreactor applications problematic.

A further problem of known mixing chambers is that when the mixing chamber occupies all or most of the reactor vessel floor area, there is no or limited room for the sludge discharge system on or near the reactor vessel floor.

Furthermore, the mixing chamber from EP0539430B1 has a outlet system for bringing material from the mixing chamber into the reaction chamber that is a slit which runs from the bottom of the mixing chamber to the top. As such, material is inserted along the full height of the mixing chamber. As was mentioned before, ideally the influent or mixture of influent and recycled material is inserted into the reactor vessel as close to the reactor vessel bottom as possible. Known mixing chambers which have outlets over the full height of the mixing chamber are therefore not optimal.

It is an object of the invention to overcome one or more of these problems.

To this end, the invention provides a bioreactor comprising a reactor vessel having a mixing chamber separated by a partition from a reaction chamber located generally above the mixing chamber, the mixing chamber having an inlet system for influent or a mixture of influent and recycled material and an outlet system for bringing material into the reaction chamber, and wherein the partition is formed from plates supported by a skeleton formed by skeleton elements, wherein the skeleton elements lie essentially along the partition sides. By providing skeleton elements extending along the partition, a cost effective support is provided along the partition.

A mixing chamber according to an embodiment of the invention comprises a house. It can be formed essentially as a box having a floor, sides forming walls and optionally a roof. The walls and optionally the roof form the partition with the reaction chamber.

In an embodiment the house occupies a limited area of the floor or bottom of the reactor vessel/reaction chamber. This will allow sludge to deposit adjacent the house, limiting the weight of collected sludge on the house of the mixing chamber. A skeleton in combination with a limited use of the bottom surface area is a cost effective solution.

One way to overcome the problem that certain cost effective materials to be used for the walls and roof of a mixing chamber are not strong enough, is to fortify the structure with a skeleton or framework. However, it is important that flow patterns inside the mixing chamber are not limited by the elements of this skeleton, since that would hamper the mixing process. A preferred way to strengthen the structure is thus to provide it with a skeleton of strong enough materials that will support plates forming the walls and roof of the structure, where the skeleton elements, such as for example ribs, support bars, and rafter-like supports, that make up the skeleton are essentially in the same plane as the plates that make up the walls and roofs, so that the skeleton elements do not hamper the flow of materials inside the mixing chamber.

In an embodiment the skeleton comprises skeleton elements positioned along plate-like parts of the partition for locally supporting the partition. The skeleton elements can comprise bars. Bars hamper flows in a limited way.

In one direction parallel to the floor the box will be larger than in another, perpendicular, direction parallel to the floor. The first direction will be called the length of the chamber and the second direction the width. The distance between planes (mostly) coinciding with the floor and the roof or topmost point of the mixing chamber will be called the height. It is advantageous to construct and arrange said skeleton for example in the form of regularly placed elements, preferably along the length axis, where the elements are for example support beams, pillars, arches, or rafters, which provide a sturdy framework to which plates can be connected. All plates together then form the partition between mixing chamber and reaction chamber. The plates can be connected on the outside of the skeleton or on the inside, where inside means towards the interior of the mixing chamber, or connected between the skeleton parts. In a preferred embodiment according the invention, the skeleton elements comprises rafters placed at mutual distances along the length of the mixing chamber. The rafters form supports that the plates that form the partition can be attached to. Placing the rafters in a regular fashion along the longest axis of the structure has the advantages of evenly distributing the load on the skeleton and allowing the use of fixed plate sizes along the axis.

In a further preferred embodiment, the skeleton is an exo-skeleton, meaning the plates are attached to the sides of the skeleton elements that essentially face the mixing chamber. This has the advantage that the interior of the partition, facing the mixing chamber, can be essentially smooth which can be beneficial to the mixing. Furthermore, the system is thus more robust for occasional over pressure inside the mixing chamber compared to the pressure of the surrounding reaction chamber. This may for example occur when there are high concentrations of gaseous materials in the influent or in the fluid from the downer.

In a further preferred embodiment according the invention, the plates that extend from the bottom of the mixing chamber have an angle with respect to the mixing chamber bottommost plane which is between 45 and 85 degrees, preferably between 55 and 75 degrees. The advantage of non-vertical walls, by arranging the walls at less than 85, preferably less than 75 degrees angle with respect to the bottommost plane, is that doing so reduces the area of the roof of the mixing chamber compared to the floor of the mixing chamber. A reduced area of the roof allows less sludge to settle there. However, the tilt of the walls must not become too small, otherwise the sludge will settle on the walls as well. Therefore, a minimum angle of 45 degrees, preferably 55 degrees, with respect to the bottommost plane is advantageous.

In a further preferred embodiment according the invention, the plates have one or more openings that are at a distance d from the bottommost plane of the mixing chamber, where distance d is less than half the difference between bottommost and topmost planes of the mixing chamber. As was mentioned before, it is advantageous to insert the mixture of influent and recycled material into the reaction chamber as close as possible to the reaction chamber floor.

In order to have optimal conditions for interaction between said mixture and the sludge in the reaction chamber, in a further preferred embodiment according the invention the mixing chamber is positioned on a reactor bottom of the reactor vessel and the openings in the partition are directed generally parallel to the reactor bottom.

When the mixing chamber, or collection of mixing chambers, in the reaction vessel do not occupy the full area of the reactor bottom, then there is room to position a sludge discharge system at the location where the most sludge will accumulate, i.e. at the bottom of the reactor. Therefore, in a preferred embodiment of the invention the reactor vessel further comprises a sludge discharge system that is positioned on or near the reactor bottom of the reactor vessel.

It is especially advantageous when the sludge discharge system is positioned at essentially the same distance from the reactor vessel floor as the openings in the mixing chamber partition.

In an embodiment according the invention, the reactor vessel comprises at least two mixing chambers on the floor of the reaction chamber, where the area of said floor occupied by mixing chambers is less than half the total area of said floor, leaving enough room for the sludge discharge system. Furthermore, the mixing chambers have openings for bringing mixture material into the reaction chamber. For optimal mixing, it is advantageous to have given the stream of mixture material coming from these openings a certain direction. In a preferred embodiment, this can be achieved when the plates have one or more openings that are formed by pieces of pipe that are oriented in a direction that is mainly perpendicular to the surface of the plates. By orienting the direction of the pieces of pipe, for example by changing the orientation of the tubes with respect to the mixing chamber wall in which they are placed or by adjusting the orientation of the entire mixing chamber inside the reactor vessel, the streams of the incoming mixture can be determined by the designer of the bioreactor, and set to allow for optimal reactor efficiency.

In an embodiment according the invention, the mixing chambers are fastened to the floor of the reaction chamber by affixing the mixing chamber or the skeleton to base plates using for example bolts, and which base plates are in turn welded, bolted, or otherwise secured to the reaction chamber floor.

It may occur that the pressure inside the mixing chamber rises to undesirable levels, for example due to blockages in the openings for bringing material into the reaction chamber or due to high concentrations of gasses in the influent material which collect at the top of the mixing chamber. To relieve excess pressure, there may be a gap between the floor of the reaction chamber and the lower edge of the mixing chamber plates. This gap may for example have the same height as the base plates that the mixing chamber skeleton is affixed on. This gap helps to keep the liquid pressure inside and outside the mixing chamber about equal, typical pressure differences being about 0.5 meters of water pressure (0.05 bar). Base plates can be provided at a mutual distance from each other.

In a preferred embodiment the mixing chamber outlet system further comprises an additional outlet means configured to transport gaseous materials in the influent or in a mixture of influent and recycled material to the reaction chamber. Said outlet means may be in the shape of an upside-down U, so that gaseous compounds can escape into the reaction chamber, but no liquid or sludge material from the reaction chamber is injected back into the mixing chamber. Alternatively, the outlet may be arranged in the form of a valve. It is advantageous to place the outlet near the top of the mixing chamber, since this is where gaseous material will accumulate.

In an embodiment and/or according to another aspect of the invention a mixing chamber is provided without a skeleton from more rigid materials. Therefore, an embodiment of the invention is a bioreactor comprising a reactor vessel having a mixing chamber separated by a partition from a reaction chamber located generally above the mixing chamber, the mixing chamber having an inlet system for influent or a mixture of influent and recycled material and an outlet system for bringing material into the reaction chamber, and wherein the mixing chamber has walls at an angle between 45 degrees and 85 degrees, preferably between 55 degrees and 75 degrees, with the reactor vessel's floor, and wherein the mixing chamber has a roof part which is connected to a downer tube. Said bioreactor may be combined with advantageous features mentioned in the preceding text.

A preferred embodiment of the mixing chamber according to this aspect comprises a mixing chamber formed as a house, occupying a limited area of the surface area of a bottom of the reactor vessel. This will allow sludge to deposit adjacent the mixing chamber house and in an embodiment will allow removing the sludge at (regular) intervals using a sludge removal system, formed and positioned on the bottom of the reactor vessel not occupied by the mixing chamber. This will allow to reduce the pressure/weight of sludge on the mixing chamber, allowing construction of the mixing chamber using less material.

Although specific embodiments will be described in this disclosure, it will be clear for the skilled person, that the invention is not limited to the specific embodiments. Any of the features described in this disclosure, including the features described with an explicit advantage as well as features having implicit advantages are comprised in this disclosure and can be part of claimed subject matter, in particular of divisional applications.

It is known that in wastewater treatment a number of methods exists. One of the choices is the manner in which the digestion of organic matter in the wastewater is arranged. This can be done for example through anaerobic digestion, which is a bacterial process that is carried out in the absence of oxygen, or aerobic digestion, which is a bacterial process in the presence of oxygen. Under anaerobic conditions, fermentation takes place in the reaction chamber as a result of contact between sludge granules and water soluble substances, such as lower fatty acids, and methane is formed.

Figure 1:
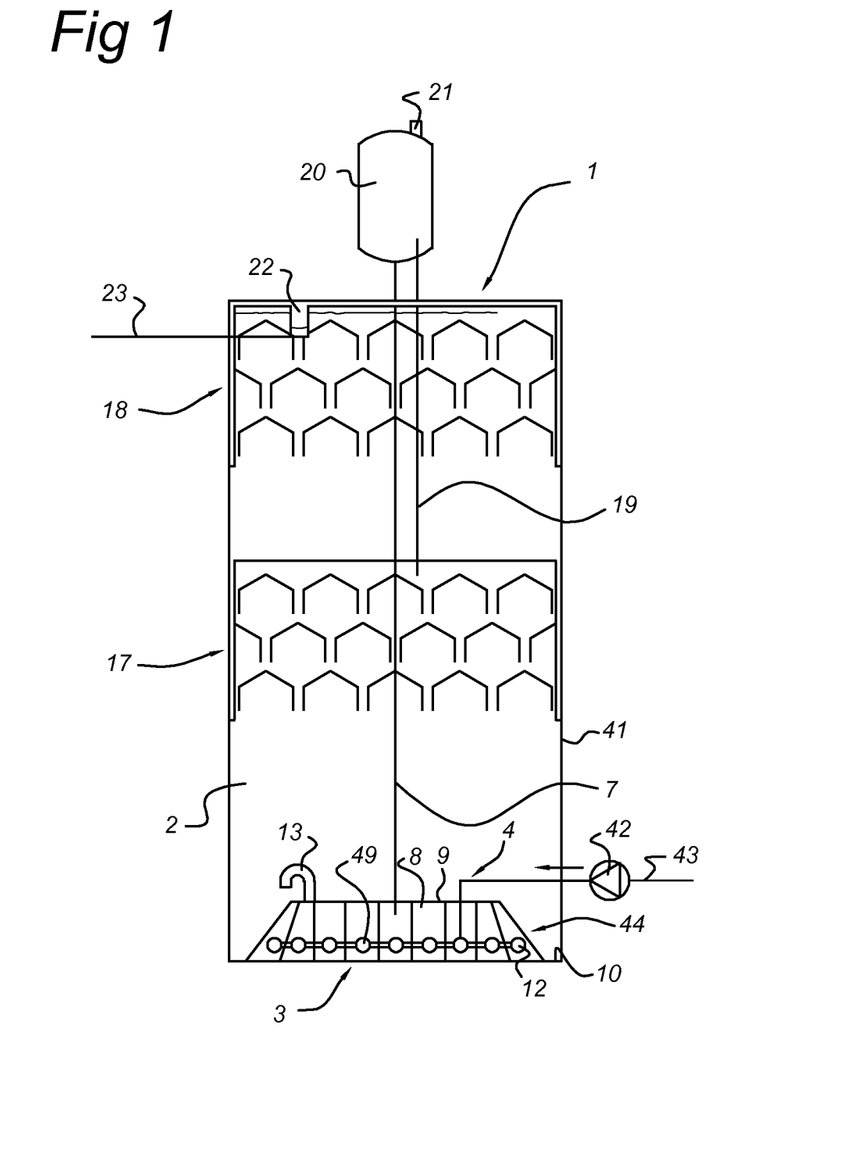
FIG. 1 shows a vertical cross section of a bioreactor.

The bioreactor 1 shown in FIG. 1 is an anaerobic waste water treatment installation, comprising a reactor vessel 41, inside which is a reaction chamber 2. As is known, a wide range of reactor sizes is possible. Dimensions for reactor vessels 41 are about 8-30 meters in height, and 3-15 meters in diameter. Typical dimensions for anaerobic waste water treatment vessels 41 are 20-30 meters of height, and 5-15 meters of diameter. Inside the reaction chamber 2, the contaminated fluid interacts with sludge and in particular the anaerobic bacterial processes take place there. On the floor 10 of the reaction chamber 2, there is at least one mixing chamber 3, which mixes incoming influent material with partially recycled material. The mixing chamber 3 is designed to introduce a fluid mixture into the reaction chamber 2 for processing. Each mixing chamber 3 receives influent material via an inlet system 4. Influent is pumped 42 from outside into the mixing chamber 3 and is distributed by pipes 43.

The inlet system 4 also comprises the downer 7 connected to the mixing chamber 3. The downer 7 brings recycled material from the higher regions of the bioreactor 1 back into the mixing chamber 3. After it is mixed with the influent material the mixture of new and partially recycled material is brought back into the reaction chamber 2. There is typically one downer 7 for each mixing chamber 3 in the reaction chamber 2.

The mixing chamber 3 in the shown embodiment is essentially box-shaped, with a partition 44 between mixing chamber 3 and reaction chamber 2. The partition or membrane 44 is typically formed by plates 8, for example made of plastic, such as polypropylene. The roof 9 and floor of the mixing chamber 3 are essentially parallel with the reactor vessel floor. However, it is possible to envision designs without a roof, for example in a conical or pyramid shape, and/or without a floor, for example an upside-down pyramid or funnel shape.

As can be seen in FIG. 1, the reactor vessel floor 10 is essentially the same as the reaction chamber floor. In this description, the two terms will be used interchangeably.

Round openings 49 are provided in the plates 8 forming a fluid connecting between the mixing chamber 3 and reaction chamber 2, forming the outlets of the inlet system 4 into the mixing chamber 3. The outlets of the inlet system 41 comprises in this embodiment a number of small pipes 66 (not shown in FIG. 1, refer to FIG. 2*c*) extending through partition 44 with circular cross sections 12. From inlet system 4 influent is brought into the mixing chamber 3 by exiting through the outlets of the inlet system 4. From the mixing chamber the fluid can enter the reaction chamber 2 through openings 49.

Although many other types of openings 49 for bringing material from the mixing chamber into the reaction chamber are possible, the advantage of the pipes is that the out-flowing material is directed generally along the length of the pipes 66. This allows the designer of the bioreactor to set up the positions and locations of the tubes in such a manner as to obtain optimal conditions for the reactions in the reaction chamber.

The pipe 66 extends somewhat internally of the plates 8 inward into the mixing chamber and extends somewhat from the outside of plates 8 into the reaction chamber 2. As sludge can deposit on the mixing chamber 3, the collected sludge falls/slide over the tube 66 and does not block the pipe exits.

In a preferred embodiment, the outlets of the inlet system 4 further comprises one or more gas relieve systems 13, which bring gaseous material out of the mixing chamber 3 into the reaction chamber 2. It is advantageous to locate the relieve system 13 on the roof 9 of the mixing chamber 3, since gaseous material will rise to the top of the mixing chamber 3. Other pressure relieve systems 13 than the one shown in FIG. 1, for example valves, will be known to a skilled person. The relieve system 13 preferably has the shape of an upside down U, to prevent sludge materials from the reaction chamber entering the mixing chamber.

Features of the mixing chamber will be discussed in more detail in connection with FIGS. 2 and 3.

The outlets of the inlet system 4 transfers a fluid mixture of the influent and recycled material into the reaction chamber 2 through partition 44. Inside the reaction chamber 2 the anaerobic reactions will take place. As the influent material is being processed, lighter materials, such as gasses and liquids, will generally rise in the reaction chamber 2.

In the embodiment according to FIG. 1, the bioreactor 1 comprises a first stage collection system or separator 17 which is arranged to collect mainly gaseous and liquid materials. A second stage collection system or separator 18 is provided as well. Both collection systems 17 and 18 bring material, via interconnecting riser 19 in the case of the first stage, into the separation chamber 20. This separation chamber 20 will separate gaseous materials from the rest of the material. The gaseous material can exit the chamber via biogas outlet 21. The other materials are collected in the downer 7 and transported, via the inlet system 4 back into the mixing chamber 3. Thus the mixing chamber 3 mixes influent material and partially recycled material. Downer 7 and interconnecting riser 19 are schematically indicated by a line.

In the FIG. 1, the downer 7 is attached to the roof 9 of the mixing chamber 3. It may be that the mixing chamber 3 supports the downer 7, or the downer 7 helps to support the mixing chamber 3. Other ways to connect the downer 7 to the mixing chamber 3 are possible as well, for example through an inlet in the side of the mixing chamber 3. In an embodiment of the invention, not shown in FIG. 1, some or all of the influent material is inserted into the downer 7 somewhere between the separation chamber 20 and the mixing chamber 3 and from there transported to the mixing chamber 3.

The reaction chamber 2 further comprises an effluent outlet system 22, for outlet or cleaned liquid materials. The effluent outlet system 22 is a collection system and accumulates outlet fluids from the reaction chamber 2, which can then exit the bioreactor via effluent discharge 23. The effluent outlet system 22 is shown only schematically.

In the embodiment according to FIG. 1 there are three ways for material to leave the reaction chamber 2. First, cleaned fluids can leave the system through the effluent outlet system 22. Second, a mixture of gas and fluids can enter one of the collection system stages 17 or 18. In this case, the gaseous material will exit the bioreactor through the biogas outlet 21, and the other materials will be sent back to the mixing chamber via downer 7. Third, a mixture of fluid and solid materials may be removed through a sludge discharge system (not shown in FIG. 1).

Figure 2A:
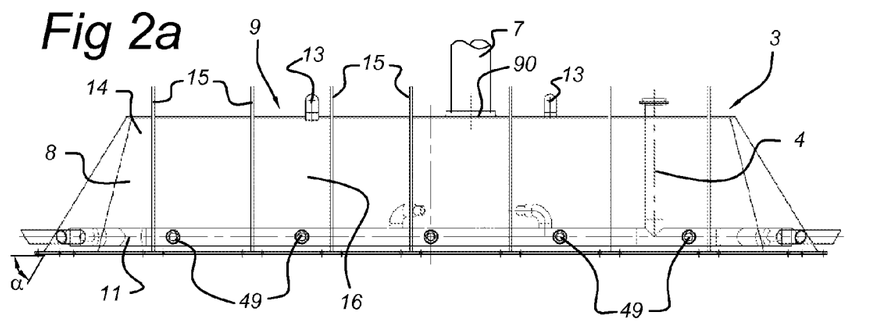
FIGS. 2a-2d show cross sections and details of a mixing chamber.
Figure 2B:
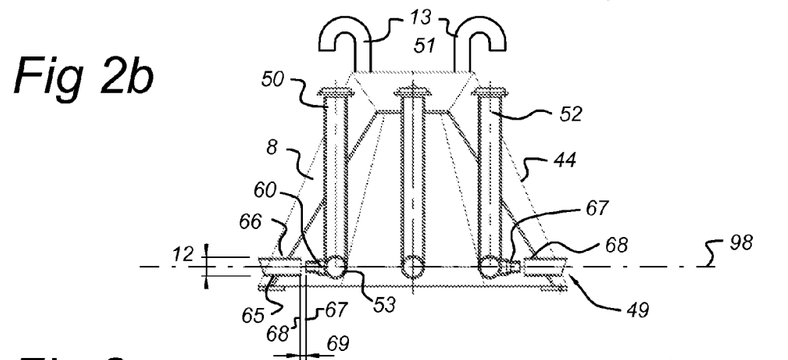
Figure 2C:
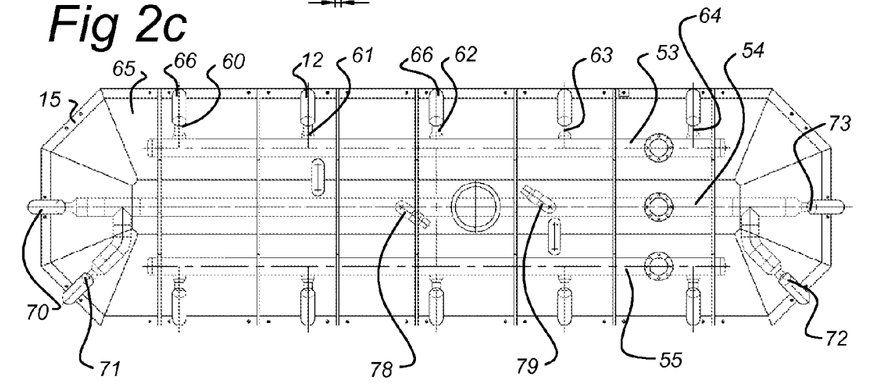

FIGS. 2a-2c show 3 cross sections of the mixing chamber, a front view (2a), a side view (2b) and a top view (2c).

Mixing chamber 3 of FIG. 2 comprises an inlet system for influent or a mixture of influent and recycled material 4 connected to a pump 42 located outside the bioreactor 1. The inlet system 4 allows influent to enter the bioreactor 1 and in particular the mixing chamber 3.

Figure 2D:
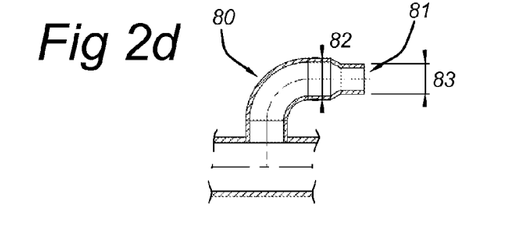

From a pump 42, according to the embodiment shown in FIG. 2d, the three pipes 50, 51, 52 enter the reactor vessel 41. The pipes 50-52 are connected to and enter the mixing chamber 3, running through openings in the partition 44. The pipes 50-52 are connected to distribution pipes 53-55, shown in detail in FIG. 2c. The distribution pipes 53-55 extend over the bottom 10 of the reactor vessel 41, more or less in a horizontal plane. The influent inlet system 4 comprises pipes 50-52 and 53-55, and downer 7. It will be obvious to a skilled person that an influent inlet system 4 can be arranged using a different number of pipes, and/or pipes in a different arrangement than shown in the figures. For example, the influent material may enter the mixing chamber through pipes that all run through the sides of the chamber partition instead of having one pipe, 51, running through the roof 9.

Distribution pipes 53-55 each have a number of outlets or exits. Distribution pipe 53 has five outlets for the influent. The outlets are formed by nozzles 60-64. Nozzle 60 is shown in side view in FIG. 2b. The nozzles 60-64 are directed at the partition 44 which is provided with openings, here in the form of pipes 66. The influent enters the mixing chamber 3 in order to allow mixing with fluid already present in the mixing chamber 3. Further as a results of the direction of the nozzles 60-64 at the partition 44, fluid from the mixing chamber will be drawn with the influent into the pipes 66 out into the reaction chamber 2.

In an embodiment pipes 66 shown in cross-sectional view in FIG. 2b, extend from inside the mixing chambers though partition 65 and extending outwards from partition 44 into the reaction chamber 2.

The influent inlet system 4 further comprises the distribution pipe 55 also having five nozzles directed in the opposite direction towards partition in the opposite direction from partition 44.

Distribution pipe 54 has four nozzles 70-73 directed in opposite directions, also directed at other partition walls having openings for fluid from the mixing chamber 3 to exit through the openings into the reactor chamber 2.

A free space 69, indicated in FIG. 2b, between a nozzle end 67 and a proximal end 68 of pipe 66 through the partition, forms a free path for the influent from nozzle 60 through [[t]] the mixing chamber 3.

As influent is fed into the mixing chamber 3, it will be accelerated by the nozzle 60-64, said nozzle having a reduction of surface area for exiting fluid/influent into the mixing chamber. A detail of an embodiment of a nozzle 80 is shown in FIG. 2d showing a surface area reduction of at least 20%, here about 50%, at the exit end 81 of the nozzle 80 with respect to the surface area of the distribution pipe. Diameter 83 is at least 10% smaller then diameter 82.

The free passage 69 is in an embodiment about 20-80 mm, preferably 30-50 mm. The diameter 83 of nozzle ends 81 is preferably about 70-120 mm. In an embodiment the diameter of pipe 66 is about 120-180 mm.

The exit end 81 of the nozzle is directed at opening 68 of pipe 66, said pipe having a surface area larger, preferably about 30%, more preferably about 50% larger than the surface area of the nozzle end 69, 81.

As influent is fed into the mixing chamber 3 at the nozzle ends 67, it will pull or draw fluid from the mixing chamber as a result of its velocity. The mixture of influent and fluid from the mixing chamber 3 flows into the open end 68 of pipe 66. Mixing of the influent and fluid from the mixing chamber 3 is the result of using the inlet energy of the influent. Further the inlet energy is provided directly as energy for the mixture flow into the reactor chamber 2.

The centerlines 98 of pipe 66 and nozzle 60 are generally aligned.

Further distribution pipe 54 is provided with nozzles 78, 79 directed tangentially with respect to downer 7 in order to provide a spiraling flow of the recycled mixture entering the mixing chamber 3 from the downer 7 and part of the influent entering the mixing chamber from pump 41.

FIG. 2*a* further shows the flange 90 arranged on roof 9 for connecting the downer 7 with the roof 9. Using a flange 90 allows quickly connecting the downer 7 to the roof, saving costs.

It is advantageous to construct the mixing chamber from relatively inexpensive materials such as plastics, in particular polypropylene or polyethylene. However, in order for the chamber to have the needed strength to resist the outside pressure, mostly due to sludge settling on top of it, according to the invention a number of measures are taken.

In the embodiment according to FIG. 2 the mixing chamber 3 comprises a partition 44, here plastic plates 8 arranged together to form the walls and roof 9 of the mixing chamber, to which a support structure or skeleton 14, here an exo-skeleton in the form of rafters or ribs 15, is fastened. This measure has the effect of fortifying the structure, so that it is better able to withstand the pressure from any sludge on top of it. In an embodiment metal rafters 15 are used. In another embodiment the rafters also formed from plastics. By using rafters/ribs as skeleton or support frame, it becomes possible to use plastic as the only material for forming the mixing chamber 3.

In another embodiment the house of the mixing chamber 3 itself is self-supporting, e.g. by using metal plates for the partition.

FIG. 2*a* shows side views of 7 rafters 15 distributed along the length of the mixing chamber 3. FIG. 2*b* shows a cross section of one such rafter 15. Thus, in a preferred embodiment the straight parts that make up the side walls and roof 9 lie along the plates 8 that form the walls and roof 9, and thus do not disturb the flow inside the mixing chamber 3. The rafter parts 15 may be attached on the inside of the plates 8, or on the outside. It is advantageous to attach the rafters 15 on the outside of the plates 8, so that the inside of the mixing chamber partition is flat and smooth, to allow optimal mixing. This forms an exo-skeleton. Further the exo-skeleton strengthens the mixing chamber if an overpressure occurs.

An embodiment utilizes two materials for the mixing chamber 3 structure, a first, more rigid, material for the supporting structure 14 and a second, more flexible, material for the partition 44 formed by plates 8. Another embodiment is to create the entire structure of walls and roof in a self-supporting form, removing the need for a support structure, but increasing the demands (and likely the costs) of the used material. Steel plates can be used to manufacture the house of the mixing chamber 2.

As a second measure to resist pressure forces from the reaction chamber 2, the roof 8 and walls 9 are shaped advantageously with regard to sludge deposits. The roof 9 is made relatively small, that is, it has a relatively small surface area seen in a top view. In the embodiment according to FIGS. 1 and 2 the mixing chamber 3 has a roof 9 that occupies less than 30%, preferably less than 20% of the total surface area of the surface area of bottom 10. Only a relatively small amount of sludge can deposit on the roof 9.

By using an exo-skeleton, rafters 15 are arranged over the roof 9 forming flow guides that will allow sludge to be guided away from the roof 9.

Still the roof is arranged generally large enough to support the connection means, such as flanges, of the inlet system (see FIG. 2C). The walls 8 are put at an angle alpha with respect to the floor of the reactor vessel 41 on which the reaction chambers 2 are placed. An advantageous angle is at least 45 degrees, preferably between 55 and 75 degrees. Higher angles, such as close to 90 degrees are disadvantageous, as this will mean the roof area 9 will increase more, so that sludge may settle there. It is ideal that the slope of the walls 8 is steep enough to prevent sludge from settling there, but not steeper, e.g. between 55 and 75 degrees. This ensures that most of the sludge that attempts to settle on the mixing chamber 3 will slide down to the reactor vessel floor 10. This is advantageous from the point of view of the stresses on the mixing chamber 3, and from the perspective of the operation of the bioreactor 1, which functions best if there is maximum height separation between heavy materials, near the floor 10, and the lighter materials above.

The mixing chamber 3 is attached to the floor 10 of the reactor vessel 41 with pins or screws through the holes in the chamber's bottom strip 15. It will be clear to a skilled person that a multitude of ways exist to attach the mixing chamber 3 to a vessel floor 10. In an embodiment according the invention, the mixing chambers are fastened to the floor of the reaction chamber by affixing the bottom strip 15 to base plates using for example bolts, and which base plates are in turn welded, bolted, or otherwise secured to the reaction chamber floor. There may be a gap between the floor of the reaction chamber and the lower edge of the mixing chamber plates 8. This gap may for example have the same height as the base plates that the mixing chamber skeleton is affixed on.

Figure 3A:
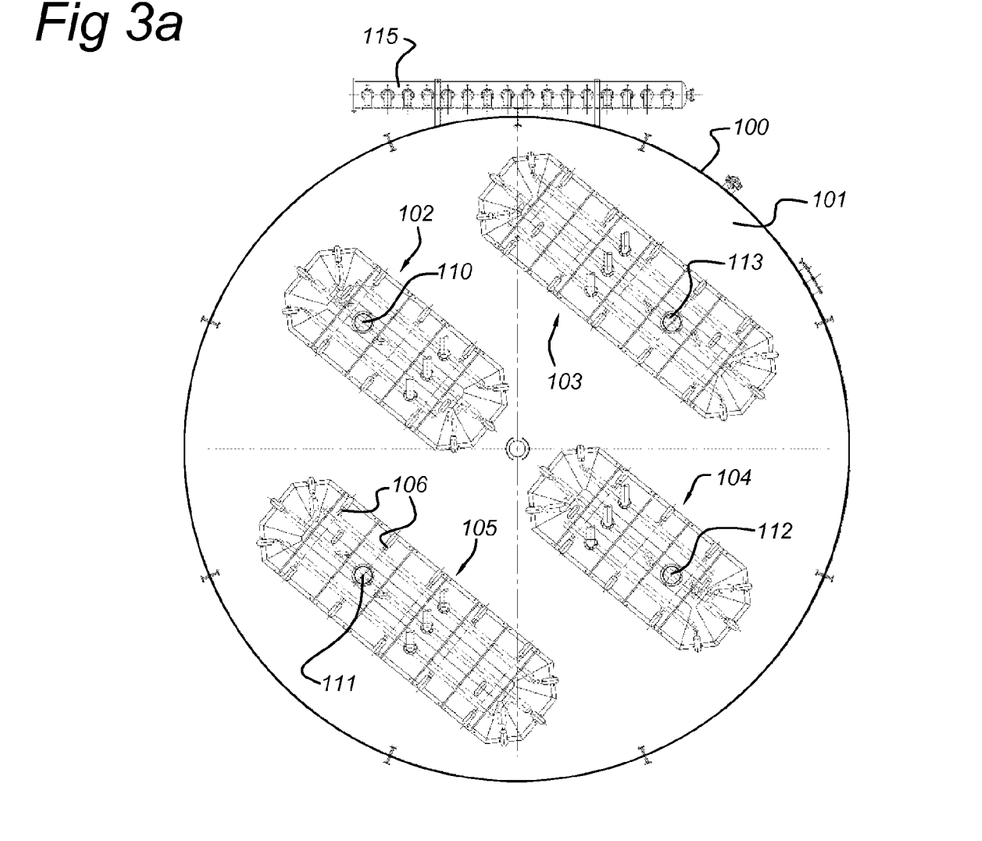
FIGS. 3a-b show a top down view of mixing chambers inside a reaction chamber.
Figure 3B:
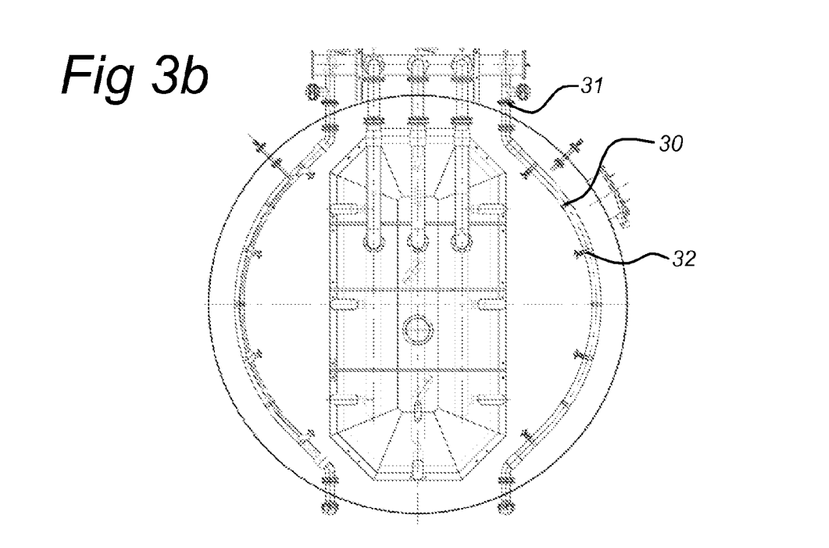

A third measure to reduce the effect of sludge weighing down on the mixing chambers 3 formed as houses according to an aspect of the invention, is illustrated in FIG. 3, which shows a top down view of 4 mixing chambers on the floor of a reaction chamber in a cylindrical vessel 1. In this text, the floor of the reaction chamber 2 and the floor 10 of the reactor vessel 41 are synonymous, and refer to the surface that the mixing chambers are placed on. As can be seen in FIG. 3, the total reaction chamber floor area 10 occupied by all mixing chambers 3 together is typically less than half of the total floor area 10 and the locations of the mixing chambers 3 on the floor 10 is distributed evenly. Therefore, most of the sludge will settle on the floor 10 immediately, some will end up on the floor by sliding off the inclined walls, and only a small fraction of the sludge will rest on the roofs 9 of the mixing chambers 3. Compared to mixing chambers 3 that are known, such as for example the conical structure of EP0539430B1 which spans the entire floor of the reactor 41, this means that the forces exerted on the mixing chamber structures 3 are much reduced, and therefore that the structures can be created with lighter and more cost-effective materials.

It therefore can be, also depending on total area and the ratio of mixing chamber volume to reactor vessel volume, more advantageous to have more than one smaller mixing chamber 3, than one large one. This ensures that there is enough floor area available for most of the sludge to settle on, and means that there is enough available floor area to direct the outlet system tubes 12 to, so that optimal reaction conditions are obtained.

FIG. 3*a* shows a cross-sectional view of a different bioreactor having a reactor vessel 100 having a floor 101 and having a diameter of about 15 meter. In such an arrangement according to FIG. 3*a* the bottom 101 is provided with four mixing chambers 102-105 distributed over the floor surface 101. Mixing chambers 103 and 105 have about the same size while chambers 102 and 104 have about the same size. Mixing chambers 102-105 are structured more or less similar to the house of mixing chamber 103 according to the FIGS. 2a-2c.

The house of a mixing chamber 102-105, but also mixing chamber 3 is preferably about 2-3 meters wide and can have a length varying between 4-9 meters. Rafters are positioned preferably at mutual distances along the length of the mixing chamber, the rafter extending and supporting the house in the width direction.

A mixing chamber according to the invention comprises a boat like shaped house. Such a house can be pre-formed in a manufacturing step. This will allow a modular buildup of the bioreactor. Further constructing a boat-like shaped mixing chamber save a lot of construction time with respect to the state of the art and allows cost savings. Further the boat-like structure allows forming a roof to which the downer can be connected.

As can be seen from the top view according to FIG. 3a, the pipes 106 through the partition of the respective mixing chambers 102-105 are directed away from the mixing chambers 102-105 in generally all four directions. This will allow feeding fluid from the mixing chambers 102-105 into the reactor chamber generally parallel to the bottom surface 101 allowing some mixing in the reactor chamber. Further sludge that will deposit on the bottom 101 will be disturbed and will be reused and recycled as a result of the flow exiting from pipes 106 and will be reused in the reaction chamber.

The influent inlet system 115 is shown in FIG. 3a having twelve pipes connected to the distributing pipes in the mixing chambers 102-105. Distribution of the influent is generally similar to the distribution according to FIGS. 2a-2c. The pipes are preferably formed from artificial materials, such as plastics.

Downers 110-113 are connected to a roof surface having a very limited area with respect to the surface area bottom 101, said downers 110-113 allowing a distribution of the recycled material from a top of the bioreactor. Here the roof surface area is less than 10% of the total floor surface area.

Not shown in FIG. 3a, but similar to the FIG. 3b embodiment a sludge removal system can be positioned near or on bottom 101 for removing sludge that positions from the floor 101.

As the partition walls of the mixing chambers 102-105 are positioned at a relatively steep angle, sludge will not collect on the partition but will be collected at the floor 101 and the sludge removal system will be able to remove the sludge more quickly.

FIG. 3b shows a sludge discharge system 30 comprising a tube inside the reactor with inlet openings 32, and a discharge outlet 31 outside the reactor vessel. It is an advantage of the invention that the relatively small mixing chambers 3 leave enough room to place a sludge discharge system on the bottom 10 of the reactor vessel 41. It is advantageous to locate this sludge discharge system a low height, since sludge will sink to the bottom. It is furthermore advantageous to have the mixing chamber outlet openings 12 located at essentially the same height as the sludge discharge system 30.

Sludge discharge system 30 can be connected to a pump positioned outside of the vessel 41. In an embodiment the sludge discharge system comprises openings distributed over the length of the pipes of the sludge discharge system extending over the floor of the reactor vessel 41.

It is a further advantage of the current invention that the mixing chambers may be placed on the floor of a cylindrical vessel, or indeed any shape of vessel with a locally flat floor, by straightforward attachment means which are known to a skilled person, and are not otherwise structurally integrated with the surrounding vessel, as is for example the case with the conical structure in EP0539430B1 which is welded to the sides of a cylindrical vessel. When manufacturing a bioreactor according the invention, this allows the use of commercially available vessels rather than custom made bioreactor vessels, which has a significant cost advantage.

According to a further aspect the invention relates to the following clauses.

Clause 1: Bioreactor comprising a reactor vessel having a mixing chamber separated by a partition from a reaction chamber located generally above the mixing chamber, the mixing chamber having an inlet system for influent or a mixture of influent and recycled material and an outlet system for bringing material into the reaction chamber, and wherein the partition is formed from plates supported by a skeleton formed by skeleton elements, wherein the skeleton elements lie essentially along the partition sides.

Clause 2: Bioreactor according to clause 1, wherein the skeleton elements comprises rafters placed at mutual distances along the length of the mixing chamber.

Clause 3: Bioreactor according to clause 1 or 2, wherein the skeleton is an exo-skeleton, wherein plates are attached to the sides of the skeleton elements that essentially face the mixing chamber.

Clause 4: Bioreactor according to any of the clauses 1-3, wherein the mixing chamber is a house positioned on a floor of the reactor vessel, occupying a limited surface area, less than 70%, preferably less than 50%, of the floor.

Clause 5: Bioreactor according to any of the preceding clauses, wherein the plates that extend from the bottom of the mixing chamber have an angle with respect to the mixing chamber bottommost plane which is between 45 and 85 degrees, preferably between 55 and 75 degrees.

Clause 6: Bioreactor according to any of the preceding clauses, wherein the plates have one or more openings that are at a distance d from the bottommost plane of the mixing chamber, where distance d is less than half the difference between bottommost and topmost planes of the mixing chamber Clause 7: Bioreactor according to any of the preceding clauses, wherein the mixing chamber is positioned on a reactor bottom of the reactor vessel and wherein the openings in the partition are directed generally parallel to the reactor bottom.

Clause 8: Bioreactor according to any of the preceding clauses, wherein the reactor vessel further comprises a sludge discharge system that is positioned on or near the reactor bottom of the reactor vessel.

Clause 9: Bioreactor according to clause 8, wherein the sludge discharge system is positioned at essentially the same distance from the reactor vessel floor as the openings in the mixing chamber partition.

Clause 10: Bioreactor according to any of the preceding clauses, wherein the reactor vessel comprises at least two mixing chambers on the floor of the reaction chamber, where the area of said floor occupied by mixing chambers is less than half the total area of said floor.

Clause 11: Bioreactor according to any of the preceding clauses, wherein the plates have one or more openings that are formed by pieces of pipe that are oriented in a direction that is mainly perpendicular to the surface of the plates.

Clause 12: Bioreactor according to any of the preceding clauses, wherein the mixing chamber outlet system further comprises an outlet means configured to transport gaseous materials in the influent or in a mixture of influent and recycled material to the reaction chamber.

Clause 13: Bioreactor comprising a reactor vessel having a mixing chamber separated by a partition from a reaction chamber located generally above the mixing chamber, the mixing chamber having an inlet system for influent or a mixture of influent and recycled material and an outlet system for bringing material into the reaction chamber, and wherein the mixing chamber has walls at an angle between 45 degrees and 85 degrees, preferably between 55 degrees and 75 degrees, with the reactor vessel's floor, and wherein the mixing chamber has a roof part which is connected to a downer tube.

Clause 14: Bioreactor according to clause 13 in combination with any of the features of clauses 2-12.

Clause 15: Bioreactor comprising a reactor vessel having a mixing chamber separated by a partition from a reaction chamber located generally above the mixing chamber, the mixing chamber having an inlet system for influent or a mixture of influent and recycled material and an outlet system for bringing material into the reaction chamber, and wherein the mixing chamber is positioned on a floor of the reactor vessel, wherein the mixing chamber occupies a small surface area, less than 50%, of the total surface area of a floor of the reactor, and wherein a sludge removal system is positioned on or close to the floor in between the mixing chamber and interior walls of the reactor vessel.

Any of the above clauses can be used in combination with any of the features identified in the appended clause set.

The invention claimed is:

1. A bioreactor comprising:
   a reactor vessel having a mixing chamber separated by a partition from a reaction chamber located generally above the mixing chamber, the mixing chamber having an inlet system for influent or a mixture of influent and recycled material;
   wherein the inlet system has an outlet opening in the mixing chamber, the partition having an opening forming a connection between the mixing chamber and the reaction chamber;
   wherein the outlet opening of the inlet system is directed at the opening in the partition; and
   wherein the inlet system comprises a downer connected to the mixing chamber for bringing recycled material from the higher regions of the reaction chamber back into the mixing chamber, wherein the partition forms a side wall of the mixing chamber, said side wall is placed on a floor of the reactor vessel, wherein the opening is arranged in the side wall, and wherein said side wall is tilted with respect to the floor of the reactor vessel at an angle between 45 degrees and 85 degrees,
   wherein the side wall extends diagonally upward so that a bottom surface of the mixing chamber is larger than a top surface of the mixing chamber, and
   wherein the mixing chamber occupies a small surface area, less than 50%, of the total surface area of a floor of the reactor.

2. The bioreactor of claim 1, wherein the outlet opening is aligned with the opening in the partition.

3. The bioreactor of claim 1, wherein at least four outlet openings of the inlet system are directed at, or aligned with, four respective openings in the partition.

4. The bioreactor of claim 1, wherein the outlet opening has a nozzle comprising a surface area reduction.

5. The bioreactor of claim 4, wherein the reduction is at least 25%.

6. The bioreactor of claim 1, wherein a surface area of the outlet opening is at least 20% less than a surface area of the opening in the partition.

7. The bioreactor of the claim 1, wherein a distance between the outlet opening of the inlet system and the opening in partition is less than eight times a width of the cross section of the outlet opening.

8. The bioreactor of claim 7, wherein the outlet opening and/or the opening in the partition are moveably mounted in the mixing chamber in order to vary a distance between the outlet opening of the inlet system and the opening in partition.

9. The bioreactor of claim 1, wherein the opening in the partition comprises a tube extending from one side of the partition, through the partition and out of the other side of the partition.

10. The bioreactor of claim 1, wherein the opening in the partition is positioned close, within 20 centimeter, to a reactor bottom of the reactor vessel.

11. The bioreactor of claim 1, wherein the mixing chamber further comprises outflow openings of the influent inlet system that are at least partially tangentially oriented with respect to an outflow opening for a mixture of influent and recycled material, such as a downer.

12. The bioreactor of claim 1, wherein the partition comprises a side wall of the mixing chamber, and wherein the opening is arranged in the side wall, and wherein said side wall is tilted with respect to a bottom of the reactor vessel.

13. The bioreactor of claim 1, wherein the openings in the partition are directed generally parallel to the reactor bottom.

14. The bioreactor of claim 1, wherein the mixing chamber comprises at least six openings in the partition directed outwardly from the mixing chamber in four mutually generally perpendicular directions.

15. A bioreactor comprising:
   a reactor vessel having a mixing chamber separated by a partition from a reaction chamber located generally above the mixing chamber, the mixing chamber having an inlet system for influent or a mixture of influent and recycled material and an outlet system for bringing material into the reaction chamber; and
   wherein the mixing chamber is positioned on a floor of the reactor vessel;
   wherein the mixing chamber occupies a small surface area, less than 50%, of the total surface area of a floor of the reactor;
   wherein a sludge removal system is positioned on or close to the floor in between the mixing chamber and interior walls of the reactor vessel;
   wherein the inlet system comprises a downer connected to the mixing chamber for bringing recycled material from the higher regions of the reaction chamber back into the mixing chamber, and
   wherein the outlet system brings material into the reaction chamber through an opening in a side wall of the mixing chamber, said side wall is placed on the floor of the reactor vessel, and wherein said side wall is tilted with respect to the floor of the reactor vessel at an angle between 45 degrees and 85 degrees,
   wherein the side wall extends diagonally upward so that a bottom surface of the mixing chamber is larger than a top surface of the mixing chamber.

16. The bioreactor of claim 15,
   wherein the inlet system has an outlet opening in the mixing chamber; and
   wherein the outlet opening of the inlet system is directed at the opening in the side wall.

17. The bioreactor of claim 16, wherein the outlet opening has a nozzle comprising a surface area reduction;

wherein a surface area of the outlet opening is at least 20% and preferably at least 40% less than a surface area of the opening in the side wall; and wherein a distance between the outlet opening of the inlet system and the opening in side wall is less than eight times, preferably less than five times, a width of the cross section of the outlet opening.

* * * * *